United States Patent
Gough

Patent Number: 5,980,517
Date of Patent: Nov. 9, 1999

[54] CELL NECROSIS APPARATUS

[75] Inventor: Edward J. Gough, Menlo Park, Calif.

[73] Assignee: Rita Medical Systems, Inc., Mountain View, Calif.

[21] Appl. No.: 09/047,845

[22] Filed: Mar. 25, 1998

Related U.S. Application Data

[63] Continuation-in-part of application No. 09/020,182, Feb. 6, 1998, which is a continuation-in-part of application No. 08/963,239, Nov. 3, 1997, which is a continuation-in-part of application No. 08/515,379, Aug. 15, 1995, Pat. No. 5,683,384.

[51] Int. Cl.[6] .................................................. A61B 17/39
[52] U.S. Cl. .............................. 606/41; 607/101; 606/42; 606/50
[58] Field of Search .......................... 606/41, 42, 45–50; 607/100–102; 604/21, 22

[56] References Cited

U.S. PATENT DOCUMENTS

| | | |
|---|---|---|
| Re. 32,057 | 12/1985 | Leveen . |
| Re. 32,066 | 1/1986 | Leveen . |
| Re. 34,086 | 10/1992 | George . |
| 3,474,777 | 10/1969 | Figge et al. . |
| 3,834,392 | 9/1974 | Lampman et al. . |
| 3,858,586 | 1/1975 | Lessen . |
| 3,987,795 | 10/1976 | Morrison, Jr. . |
| 3,991,770 | 11/1976 | Leveen . |
| 4,011,872 | 3/1977 | Komiya . |
| 4,016,881 | 4/1977 | Rioux et al. . |
| 4,016,886 | 4/1977 | Doss . |
| 4,026,301 | 5/1977 | Friedman et al. . |
| 4,033,351 | 7/1977 | Hetzel . |
| 4,043,342 | 8/1977 | Morrison, Jr. . |
| 4,074,718 | 2/1978 | Morrison, Jr. . |
| 4,080,959 | 3/1978 | Leveen . |
| 4,085,756 | 4/1978 | Weaver . |
| 4,095,602 | 6/1978 | Leveen . |
| 4,119,102 | 10/1978 | Leveen . |
| 4,121,592 | 10/1978 | Whalley . |
| 4,140,130 | 2/1979 | Storm, III . |

(List continued on next page.)

FOREIGN PATENT DOCUMENTS

| | | |
|---|---|---|
| 0 370 890 | 5/1990 | European Pat. Off. . |
| 0 462 302 | 12/1991 | European Pat. Off. . |
| 0 472 368B1 | 2/1992 | European Pat. Off. . |
| 0 502 268 | 9/1992 | European Pat. Off. . |
| 0 519 415 | 12/1992 | European Pat. Off. . |
| 0 608 609 | 8/1994 | European Pat. Off. . |
| WO 92/10142 | 6/1992 | WIPO . |
| WO 94/04220 | 3/1994 | WIPO . |
| WO 94/10925 | 5/1994 | WIPO . |
| WO 94/11059 | 5/1994 | WIPO . |
| WO 94/17856 | 8/1994 | WIPO . |
| WO 94/25110 | 11/1994 | WIPO . |
| WO 94/26178 | 11/1994 | WIPO . |
| WO 95/19142 | 7/1995 | WIPO . |
| WO 95/25471 | 9/1995 | WIPO . |
| WO 96/04860 | 2/1996 | WIPO . |
| WO 96/29946 | 10/1996 | WIPO . |
| WO 97/06739 | 2/1997 | WIPO . |

*Primary Examiner*—Michael Peffley
*Attorney, Agent, or Firm*—Wilson Sonsini Goodrich & Rosati

[57] ABSTRACT

A cell necrosis apparatus has a flexible introducer including a lumen and a distal end sufficiently sharp to penetrate tissue. An energy delivery device is positionable in the introducer as the introducer is advanced through tissue. The energy delivery device includes a first RF electrode with a tissue piercing distal portion and a second RF electrode with a tissue piercing distal portion. The first and second RF electrodes are deployable with curvature from the introducer at a selected tissue site in a lateral direction away from the periphery of the introducer.

42 Claims, 9 Drawing Sheets

U.S. PATENT DOCUMENTS

| | | |
|---|---|---|
| 4,154,246 | 5/1979 | Leveen . |
| 4,230,129 | 10/1980 | Leveen . |
| 4,237,898 | 12/1980 | Whalley . |
| 4,269,174 | 5/1981 | Adair . |
| 4,285,346 | 8/1981 | Armitage . |
| 4,289,135 | 9/1981 | Nordensrom et al. . |
| 4,290,435 | 9/1981 | Waggott . |
| 4,303,636 | 12/1981 | Gordon . |
| 4,331,654 | 5/1982 | Morris . |
| 4,337,760 | 7/1982 | Rubin . |
| 4,345,588 | 8/1982 | Widder et al. . |
| 4,346,715 | 8/1982 | Gammell . |
| 4,375,220 | 3/1983 | Matvias . |
| 4,409,993 | 10/1983 | Furihata . |
| 4,411,266 | 10/1983 | Cosman . |
| 4,418,692 | 12/1983 | Guay . |
| 4,461,283 | 7/1984 | Doi . |
| 4,506,680 | 3/1985 | Stokes . |
| 4,512,762 | 4/1985 | Spears . |
| 4,524,770 | 6/1985 | Orandi . |
| 4,532,924 | 8/1985 | Auth et al. . |
| 4,545,368 | 10/1985 | Rand et al. . |
| 4,562,838 | 1/1986 | Walker . |
| 4,565,200 | 1/1986 | Cosman . |
| 4,574,782 | 3/1986 | Borrelli et al. . |
| 4,583,556 | 4/1986 | Hines et al. . |
| 4,586,490 | 5/1986 | Katz . |
| 4,601,296 | 7/1986 | Yerushalmi . |
| 4,648,892 | 3/1987 | Kittrell et al. . |
| 4,652,257 | 3/1987 | Chang . |
| 4,658,819 | 4/1987 | Harris et al. . |
| 4,660,571 | 4/1987 | Hess et al. . |
| 4,662,359 | 5/1987 | Gordon . |
| 4,676,258 | 6/1987 | Inokuchi et al. . |
| 4,690,130 | 9/1987 | Mirell . |
| 4,692,139 | 9/1987 | Stiles . |
| 4,709,701 | 12/1987 | Weber . |
| 4,753,248 | 6/1988 | Engler et al. . |
| 4,763,671 | 8/1988 | Goffinet . |
| 4,776,086 | 10/1988 | Kasevich et al. . |
| 4,800,899 | 1/1989 | Elliott . |
| 4,813,429 | 3/1989 | Eshel et al. . |
| 4,818,542 | 4/1989 | Deluca et al. . |
| 4,823,791 | 4/1989 | D'Amelio et al. . |
| 4,823,793 | 4/1989 | Angulo et al. . |
| 4,825,880 | 5/1989 | Stauffer et al. . |
| 4,838,265 | 6/1989 | Cosman et al. . |
| 4,846,196 | 7/1989 | Wiksell et al. . |
| 4,860,744 | 8/1989 | Johnson et al. . |
| 4,862,887 | 9/1989 | Weber et al. . |
| 4,881,543 | 11/1989 | Trembly et al. . |
| 4,887,614 | 12/1989 | Shirakami et al. . |
| 4,907,589 | 3/1990 | Cosman . |
| 4,920,978 | 5/1990 | Colvin . |
| 4,931,047 | 6/1990 | Broadwin et al. . |
| 4,940,064 | 7/1990 | Desai . |
| 4,945,912 | 8/1990 | Langberg . |
| 4,947,842 | 8/1990 | Marchosky et al. . |
| 4,950,267 | 8/1990 | Ishihara et al. . |
| 4,962,761 | 10/1990 | Golden . |
| 4,963,364 | 10/1990 | Fox et al. . |
| 4,966,604 | 10/1990 | Reiss . |
| 4,976,680 | 12/1990 | Hayman et al. . |
| 4,976,711 | 12/1990 | Parins et al. . |
| 4,983,159 | 1/1991 | Rand . |
| 4,985,022 | 1/1991 | Fearnot et al. . |
| 4,989,601 | 2/1991 | Marchosky et al. . |
| 5,003,991 | 4/1991 | Takayama et al. . |
| 5,007,908 | 4/1991 | Rydell . |
| 5,009,656 | 4/1991 | Reimels . |
| 5,010,897 | 4/1991 | Leveen . |
| 5,011,483 | 4/1991 | Sleister . |
| 5,013,312 | 5/1991 | Parins et al. . |
| 5,015,227 | 5/1991 | Broadwin et al. . |
| 5,016,615 | 5/1991 | Driller et al. . |
| 5,026,959 | 6/1991 | Ito et al. . |
| 5,047,027 | 9/1991 | Rydell . |
| 5,055,100 | 10/1991 | Olsen . |
| 5,057,107 | 10/1991 | Parins et al. . |
| 5,059,199 | 10/1991 | Okada et al. . |
| 5,067,952 | 11/1991 | Gudov et al. . |
| 5,071,419 | 12/1991 | Rydell et al. . |
| 5,078,717 | 1/1992 | Parins et al. . |
| 5,080,660 | 1/1992 | Buelna . |
| 5,083,565 | 1/1992 | Parins . |
| 5,084,001 | 1/1992 | Van't Hooft et al. . |
| 5,084,045 | 1/1992 | Helenowski . |
| 5,085,659 | 2/1992 | Rydell . |
| 5,099,756 | 3/1992 | Franconi et al. . |
| 5,100,423 | 3/1992 | Fearnot . |
| 5,115,818 | 5/1992 | Holleman et al. . |
| 5,119,832 | 6/1992 | Xavier . |
| 5,122,137 | 6/1992 | Lennox . |
| 5,125,928 | 6/1992 | Parins et al. . |
| 5,128,147 | 7/1992 | Leveen et al. . |
| 5,156,151 | 10/1992 | Imran . |
| 5,167,626 | 12/1992 | Casper et al. . |
| 5,169,396 | 12/1992 | Dowlatshahi et al. . |
| 5,170,789 | 12/1992 | Narayan et al. . |
| 5,170,805 | 12/1992 | Kensey et al. . |
| 5,178,620 | 1/1993 | Eggers et al. . |
| 5,183,455 | 2/1993 | Hayman et al. . |
| 5,190,517 | 3/1993 | Zieve et al. . |
| 5,190,539 | 3/1993 | Fletcher et al. . |
| 5,190,541 | 3/1993 | Abele . |
| 5,190,766 | 3/1993 | Ishihara . |
| 5,197,466 | 3/1993 | Marchosky et al. . |
| 5,197,963 | 3/1993 | Parins . |
| 5,197,964 | 3/1993 | Parins . |
| 5,203,353 | 4/1993 | Easley et al. . |
| 5,203,782 | 4/1993 | Gudov et al. . |
| 5,205,289 | 4/1993 | Hardy et al. . |
| 5,207,675 | 5/1993 | Canady . |
| 5,215,103 | 6/1993 | Desai . |
| 5,217,458 | 6/1993 | Parins . |
| 5,222,953 | 6/1993 | Dowlatshahi . |
| 5,236,410 | 8/1993 | Granov et al. . |
| 5,236,424 | 8/1993 | Imran . |
| 5,246,438 | 9/1993 | Langberg . |
| 5,249,585 | 10/1993 | Turner et al. . |
| 5,251,645 | 10/1993 | Fenn . |
| 5,252,922 | 10/1993 | Larson, III . |
| 5,257,451 | 11/1993 | Edwards et al. . |
| 5,258,006 | 11/1993 | Rydell et al. . |
| 5,259,394 | 11/1993 | Bens . |
| 5,259,395 | 11/1993 | Li . |
| 5,267,994 | 12/1993 | Gentelia et al. . |
| 5,273,535 | 12/1993 | Edwards et al. . |
| 5,275,162 | 1/1994 | Edwards et al. . |
| 5,277,696 | 1/1994 | Hagen . |
| 5,281,213 | 1/1994 | Milder et al. . |
| 5,281,217 | 1/1994 | Edwards et al. . |
| 5,281,218 | 1/1994 | Imran . |
| 5,282,797 | 2/1994 | Chess . |
| 5,286,253 | 2/1994 | Fucci . |
| 5,290,286 | 3/1994 | Parins . |
| 5,293,869 | 3/1994 | Edwards et al. . |
| 5,295,955 | 3/1994 | Rosen et al. . |
| 5,300,068 | 4/1994 | Rosar et al. . |
| 5,300,069 | 4/1994 | Hunsberger et al. . |
| 5,300,099 | 4/1994 | Rudie . |
| 5,304,214 | 4/1994 | Deford et al. . |

| Patent | Date | Inventor |
|---|---|---|
| 5,309,910 | 5/1994 | Edwards et al. . |
| 5,313,943 | 5/1994 | Houser et al. . |
| 5,314,466 | 5/1994 | Stern et al. . |
| 5,322,503 | 6/1994 | Desai . |
| 5,328,467 | 7/1994 | Edwards et al. . |
| 5,334,193 | 8/1994 | Nardella . |
| 5,334,206 | 8/1994 | Daikuzono . |
| 5,336,222 | 8/1994 | Durgin, Jr. et al. . |
| 5,342,357 | 8/1994 | Nardella . |
| 5,348,554 | 9/1994 | Imran et al. . |
| 5,354,296 | 10/1994 | Turkel . |
| 5,363,861 | 11/1994 | Edwards et al. . |
| 5,365,926 | 11/1994 | Desai . |
| 5,366,490 | 11/1994 | Edwards et al. . |
| 5,368,592 | 11/1994 | Stern et al. . |
| 5,370,675 | 12/1994 | Edwards et al. ............... 607/101 |
| 5,370,678 | 12/1994 | Edwards et al. . |
| 5,383,876 | 1/1995 | Nardella . |
| 5,383,917 | 1/1995 | Desai et al. ..................... 607/102 |
| 5,385,544 | 1/1995 | Edwards et al. . |
| 5,397,339 | 3/1995 | Desai . |
| 5,398,683 | 3/1995 | Edwards et al. . |
| 5,401,272 | 3/1995 | Perkins . |
| 5,403,311 | 4/1995 | Abele et al. . |
| 5,405,346 | 4/1995 | Grundy et al. . |
| 5,409,453 | 4/1995 | Lundquist et al. . |
| 5,411,025 | 5/1995 | Webster, Jr. . |
| 5,417,687 | 5/1995 | Nardella . |
| 5,421,819 | 6/1995 | Edwards et al. . |
| 5,423,807 | 6/1995 | Milder . |
| 5,423,808 | 6/1995 | Edwards et al . |
| 5,423,811 | 6/1995 | Imran et al. . |
| 5,433,708 | 7/1995 | Nichols et al. . |
| 5,435,805 | 7/1995 | Edwards et al. . |
| 5,437,662 | 8/1995 | Nardella . |
| 5,437,664 | 8/1995 | Cohen et al. . |
| 5,456,662 | 10/1995 | Edwards et al. . |
| 5,456,682 | 10/1995 | Edwards et al. . |
| 5,458,596 | 10/1995 | Lax et al. . |
| 5,458,597 | 10/1995 | Edwards et al. . |
| 5,462,521 | 10/1995 | Brucker et al. . |
| 5,470,308 | 11/1995 | Edwards et al. . |
| 5,470,309 | 11/1995 | Edwards et al. . |
| 5,471,982 | 12/1995 | Edwards et al. . |
| 5,472,441 | 12/1995 | Edwards et al. . |
| 5,484,400 | 1/1996 | Edwards et al. . |
| 5,486,161 | 1/1996 | Lax et al. . |
| 5,500,012 | 3/1996 | Brucker et al. . |
| 5,505,730 | 4/1996 | Edwards . |
| 5,507,743 | 4/1996 | Edwards et al. . |
| 5,509,419 | 4/1996 | Edwards et al. . |
| 5,514,130 | 5/1996 | Baker . |
| 5,514,131 | 5/1996 | Edwards . |
| 5,520,684 | 5/1996 | Imran . |
| 5,531,676 | 7/1996 | Edwards et al. . |
| 5,531,677 | 7/1996 | Lundquist et al. . |
| 5,536,240 | 7/1996 | Edwards et al. . |
| 5,536,267 | 7/1996 | Edwards et al. . |
| 5,540,655 | 7/1996 | Edwards et al. . |
| 5,542,915 | 8/1996 | Edwards et al. . |
| 5,542,916 | 8/1996 | Hirsch et al. . |
| 5,542,928 | 8/1996 | Evans et al. . |
| 5,545,161 | 8/1996 | Imran . |
| 5,545,171 | 8/1996 | Sharkey et al. . |
| 5,545,193 | 8/1996 | Fleishchman et al. . |
| 5,546,267 | 8/1996 | Frederiksen et al. . |
| 5,548,597 | 8/1996 | Edwards et al. . |
| 5,549,108 | 8/1996 | Edwards et al. . |
| 5,549,644 | 8/1996 | Lundquist et al. . |
| 5,554,110 | 9/1996 | Edwards et al. . |
| 5,556,377 | 9/1996 | Rosen et al. . |
| 5,558,672 | 9/1996 | Edwards et al. . |
| 5,558,673 | 9/1996 | Edwards et al. . |
| 5,560,358 | 10/1996 | Arnold et al. . |
| 5,562,703 | 10/1996 | Desai . |
| 5,599,345 | 2/1997 | Edwards et al. . |
| 5,599,346 | 2/1997 | Edwards et al. . |
| 5,609,151 | 3/1997 | Mulier et al. . |
| 5,620,481 | 4/1997 | Desai et al. . |
| 5,817,092 | 10/1998 | Behl ................................ 606/41 |
| 5,855,576 | 1/1999 | LeVeen et al. ................ 606/41 |

FIG.−1

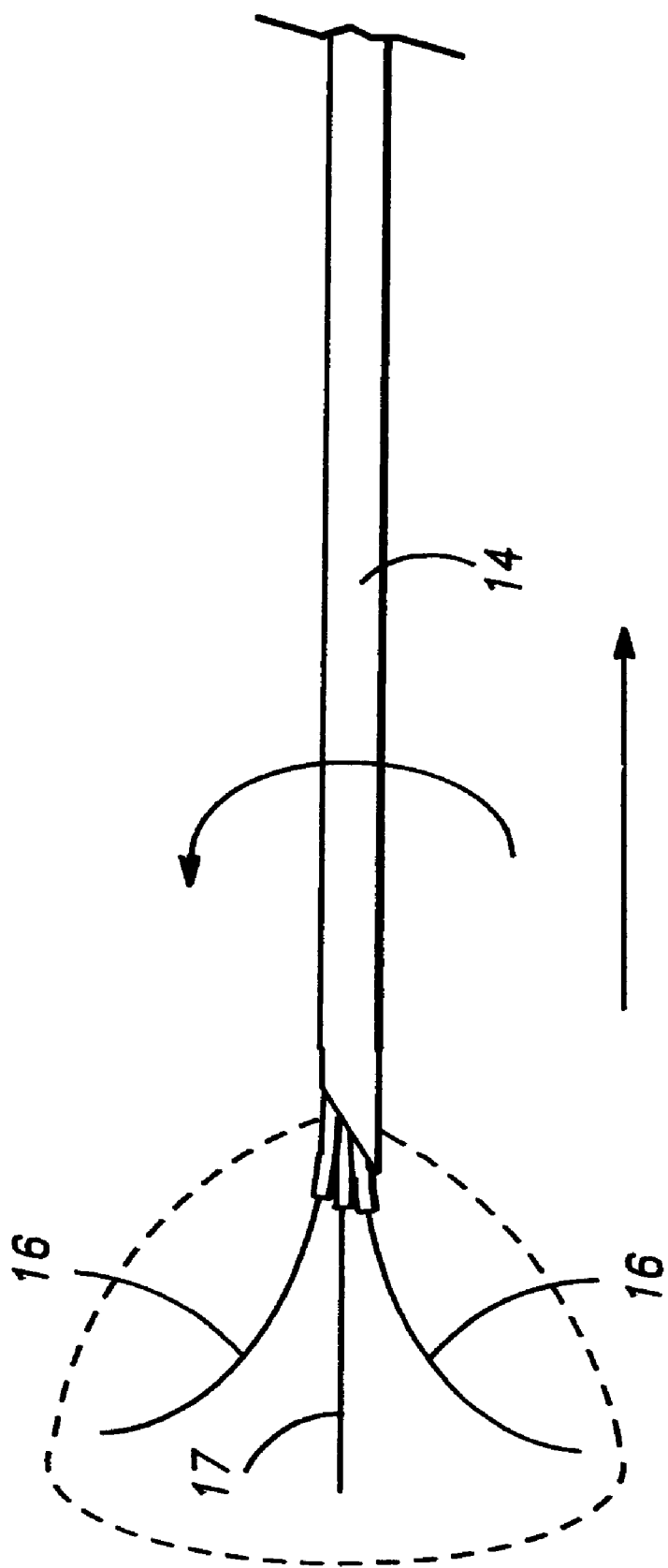

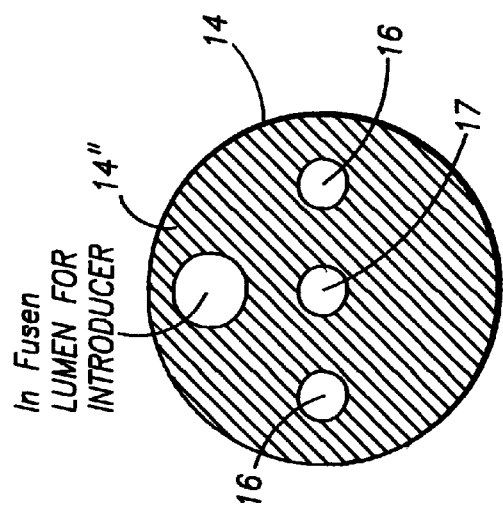
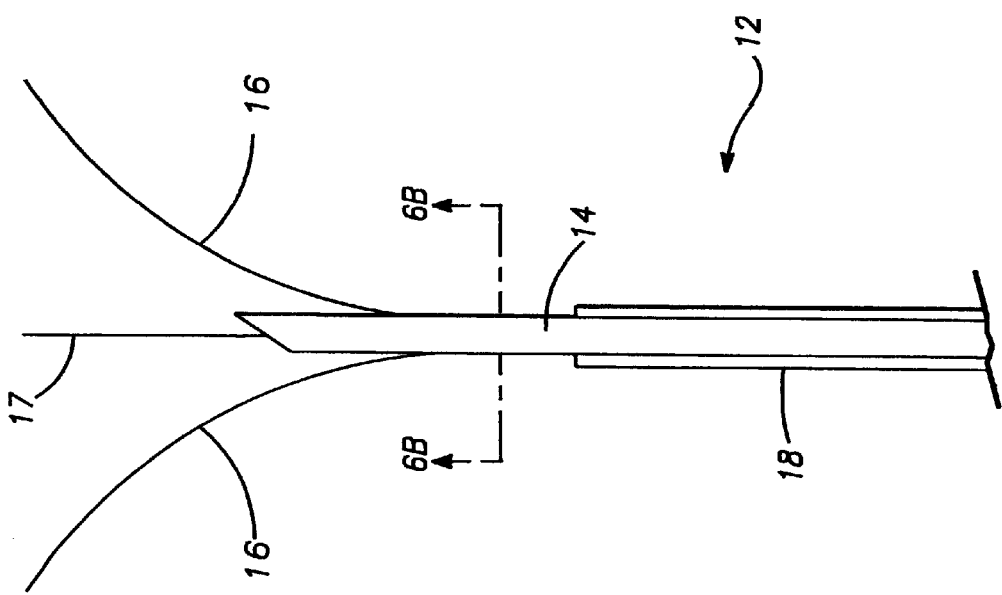

CELL NECROSIS APPARATUS

REFERENCE TO RELATED APPLICATIONS

This application is a continuation-in-part of Ser. No. 09/020,182, filed Feb. 6, 1998, which is a continuation-in-part of Ser. No. 08/963,239, filed Nov. 3, 1997, which is a continuation-in-part of Ser. No. 08/515,379, filed Aug. 15, 1995, now U.S. Pat. No. 5,683,384 all incorporated herein by reference.

BACKGROUND OF THE INVENTION

1. Field of the Invention

This invention relates generally to a cell necrosis apparatus, and more particularly to a cell necrosis apparatus with an introducer and deployable electrodes.

2. Description of the Related Art

Current open procedures for treatment of tumors are extremely disruptive and cause a great deal of damage to healthy tissue. During the surgical procedure, the physician must exercise care in not cutting the tumor in a manor that creates seeding of the tumor, resulting in metastasis. In recent years, development of products has been directed with an emphasis on minimizing the traumatic nature of traditional surgical procedures.

There has been a relatively significant amount of activity in the area of hyperthermia as a tool for treatment of tumors. It is known that elevating the temperature of tumors is helpful in the treatment and management of cancerous tissues. The mechanisms of selective cancer cell eradication by hyperthermia are not completely understood. However, four cellular effects of hyperthermia on cancerous tissue have been proposed, (i) changes in cell or nuclear membrane permeability or fluidity, (ii) cytoplasmic lysomal disintegration, causing release of digestive enzymes, (iii) protein thermal damage affecting cell respiration and the synthesis of DNA or RNA and (iv) potential excitation of immunologic systems. Treatment methods for applying heat to tumors include the use of direct contact radio-frequency (RF) applicators, microwave radiation, inductively coupled RF fields, ultrasound, and a variety of simple thermal conduction techniques.

Among the problems associated with all of these procedures is the requirement that highly localized heat be produced at depths of several centimeters beneath the surface of the skin.

Attempts to use interstitial local hyperthermia have not proven to be very successful. Results have often produced nonuniform temperatures throughout the tumor. It is believed that tumor mass reduction by hyperthermia is related to thermal dose. Thermal dose is the minimum effective temperature applied throughout the tumor mass for a defined period of time. Because blood flow is the major mechanism of heat loss for tumors being heated, and blood flow varies throughout the tumor, more even heating of tumor tissue is needed to ensure effective treatment.

The same is true for ablation of the tumor itself through the use of RF energy. Different methods have been utilized for the RF ablation of masses such as tumors. Instead of heating the tumor it is ablated through the application of energy. This process has been difficult to achieve due to a variety of factors including, (i) positioning of the RF ablation electrodes to effectively ablate all of the mass, (ii) introduction of the RF ablation electrodes to the tumor site and (iii) controlled delivery and monitoring of RF energy to achieve successful ablation without damage to non-tumor tissue.

Thus, non-invasive procedures for providing heat to internal tissue have had difficulties in achieving substantial specific and selective treatment.

Examples illustrating the use of electromagnetic energy to ablate tissue are disclosed in: U.S. Pat. No. 4,562,200; U.S. Pat. No. 4,411,266; U.S. Pat. No. 4,838,265; U.S. Pat. No. 5,403,311; U.S. Pat. No. 4,011,872; U.S. Pat. No. 5,385,544; and U.S. Pat. No. 5,385,544.

There is a need for a cell necrosis apparatus with at least two electrodes that are deployable with curvature from an introducer. There is another need for a cell necrosis apparatus with at least two electrodes that are deployable with curvature from an introducer and a third electrode which is deployable with substantially no curvature. There is yet a further need for a cell necrosis apparatus with at least two electrodes that are deployable with curvature which do not come back upon themselves.

SUMMARY OF THE INVENTION

Accordingly, an object of the invention is to provide a cell necrosis apparatus that provides tissue reduction at selected anatomical sites.

Another object of the invention is to provide a treatment apparatus to create cell necrosis.

Still another object of the invention is to provide a cell necrosis apparatus that has at least electrodes which are deployable from an introducer with curvature and a third electrode which is deployable with minimal curvature.

Yet another object of the invention is to provide a cell necrosis apparatus with a groundpad coupled to a sensor.

These and other objects of the invention are achieved in a cell necrosis apparatus with an introducer. The introducer has a distal end sufficiently sharp to penetrate tissue. An energy delivery device is positionable in the introducer as the introducer is advanced through tissue. The energy delivery device includes a first RF electrode, a second RF electrode and a third RF electrode. Each of the RF electrodes has a tissue piercing distal end. The first and second RF electrodes are deployable with curvature from the introducer. The third RF is deployable from the introducer with less curvature than the first or second electrodes.

In another embodiment, a cell necrosis apparatus includes an introducer with a distal end sufficiently sharp to penetrate tissue. An energy delivery device includes first and second RF electrodes. Both electrodes have tissue piercing distal portions and are positionable in the introducer as the introducer is advanced through tissue. The first and second RF electrodes are deployable from the introducer with curvature. A groundpad electrode is coupled to the first and second RF electrodes. A first sensor is coupled to the groundpad electrode.

BRIEF DESCRIPTION OF THE FIGURES

FIG. 5 is a perspective view illustrating the positioning of the cell necrosis apparatus in the center of a selected tissue mass, and the creation of a cylindrical ablation.

FIG. 6(a) is a perspective view of the cell necrosis apparatus of the present invention illustrating two deployed energy delivery devices with curvature which provide a retaining and gripping function.

FIG. 6(b) is a cross-sectional view of the apparatus of FIG. 6(a) taken along the lines 6(b)—6(b).

DETAILED DESCRIPTION

The present invention is a cell necrosis apparatus that includes an introducer. The introducer has a distal end sufficiently sharp to penetrate tissue. An energy delivery device is positionable in the introducer as the introducer is advanced through tissue. The energy delivery device includes a first RF electrode, a second RF electrode and a third RF electrode. Each of the RF electrodes has a tissue piercing distal end. The first and second RF electrodes are deployable with curvature from the introducer. The third RF is deployable from the introducer with less curvature than the first or second electrodes.

In another embodiment, the cell necrosis apparatus includes an introducer with a distal end sufficiently sharp to penetrate tissue. An energy delivery device includes first and second RF electrodes. Both electrodes have tissue piercing distal portions and are positionable in the introducer as the introducer is advanced through tissue. The first and second RF electrodes are deployable from the introducer with curvature. A groundpad electrode is coupled to the first and second RF electrodes. A first sensor is coupled to the groundpad electrode.

Figure 1:
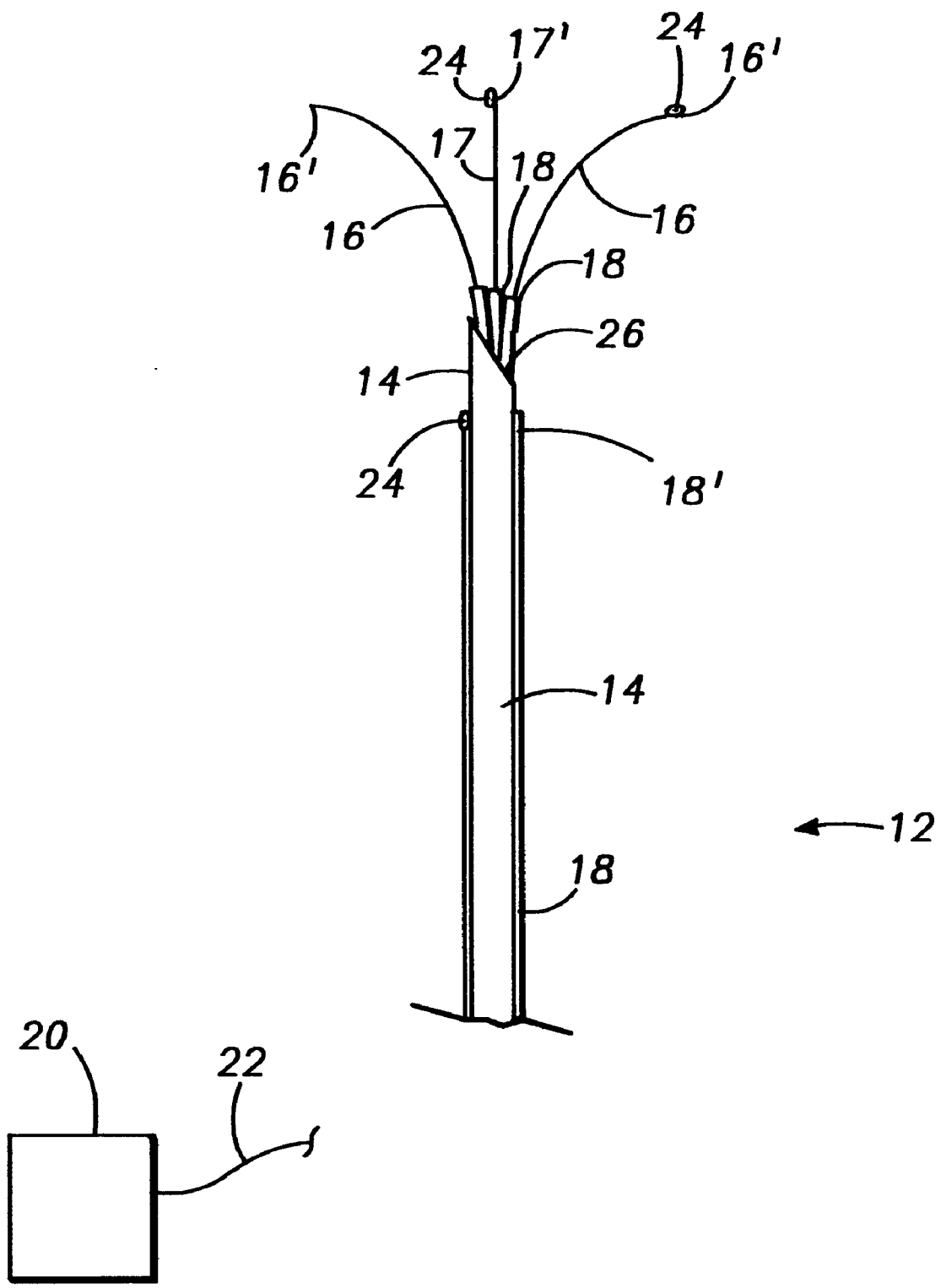
FIG. 1 is a perspective view of the cell necrosis apparatus of the present invention illustrating two deployed electrodes with curvature and a third deployed electrode with less curvature than the other two electrodes.

As shown in FIG. 1, cell necrosis apparatus 12 includes an introducer introducer 14, one or more energy delivery devices 16 that are deployed from introducer 14 with curvature. An energy delivery device 17 is deployed from introducer 14. Energy delivery device 17 is deployed with less curvature than energy delivery devices 16.

In various embodiments, energy delivery device 17 is deployable with less curvature than energy delivery devices 16 and preferably is deployed with minimal or substantially no curvature. Energy delivery devices 16 and 17 are preferably RF electrodes. Energy delivery devices 16 and 17 are initially positioned in an introducer lumen when introducer 14 is advanced through tissue. When introducer 14 reaches a selected tissue site, including but not limited to a solid lesion, energy delivery devices 16 are laterally deployed, while energy delivery device 17 is deployed with minimal curvature. Energy delivery device 17 is deployed and is surrounded by energy delivery devices 16. In one embodiment, deployed energy delivery devices 16 are positioned equally distant from energy delivery device 17. In this embodiment, energy delivery device 17 is substantially centered between energy delivery devices 16.

Volumetric cell necrosis proceeds from the interior of the selected tissue mass in a direction towards a periphery of the selected tissue mass.

Each energy delivery device has a distal end 16' which distends away from a introducer 14 in a fan like manner. Preferably, energy delivery devices 16 are deployed with curvature but without reversing their direction of travel. Distal ends 16' do not reverse their direction of travel and come back in a direction towards introducer 14. Preferably, distal ends 16' continue in a deployment direction away from introducer 14.

Unless the distal ends 16' have insulation, then their entire length of extension is an electromagnetic energy delivery surface which delivers electromagnetic energy to the selected tissue mass. The length and size of each electromagnetic energy delivery surface can be variable. Lengths of energy delivery devices 16 can be adjustable. Introducer 14 can be moved up and down, rotated about its longitudinal axis, and moved back and forth, in order to define, along with sensors, the periphery or boundary of the selected tissue mass, including but not limited to a tumor. This provides a variety of different geometries, not always symmetrical, that can be ablated. Volumetric cell necrosis is defined as the creation of cell necrosis with a periphery formed between deployed energy delivery devices 16 and 17. The volumetric cell necrosis extends outside of a area defined by the peripheries of deployed energy delivery devices 16.

The volume of non-ablated tissue between adjacent distal ends 16' is minimized. A variety of different geometric cell necrosis zones are achieved including but not limited to spherical, semi-spherical, spheroid, triangular, semi-triangular, square, semi-square, rectangular, semi-rectangular, conical, semi-conical, quadrilateral, semi-quadrilateral, semi-quadrilateral, rhomboidal, semi-rhomboidal, trapezoidal, semi-trapezoidal, combinations of the preceding, geometries with non-planar sections or sides, free-form and the like.

In one embodiment, introducer 14 has a sharpened distal end 14' to assist introduction through tissue. Each energy delivery device 16 has a distal end 16' that can be constructed to be less structurally rigid than introducer 14. Distal end 16' is the section of energy delivery device 16 that is advanced from the lumen introducer 14 and into the selected tissue mass.

Introducer 14 can be flexible. In one embodiment, introducer 14 is sufficiently flexible to pierce tissue, and move in any desired direction through tissue to a selected tissue site. In another embodiment, Introducer 14 is sufficiently flexible to reverse its direction of travel and move in direction back upon itself In one embodiment, introducer 14 is more flexible than energy delivery devices 16.

Energy delivery devices 16 and 17 can be made of a variety of conductive materials, both metallic and non-metallic. One suitable material is type 304 stainless steel of hypodermic quality. In some applications, all or a portion of energy delivery devices 16 and 17 can be made of a shaped memory metal, such as NiTi, commercially available from Raychem Corporation, Menlo Park, Calif.

Each of the energy delivery devices 16 and 17 can have different lengths. The lengths can be determined by the actual physical length of an energy delivery device 16 and 17, the length of an energy delivery device electromagnetic energy delivery surface, and the length of an energy delivery device 16 and 17 that is not covered by an insulator. Suitable lengths include but are not limited to 17.5 cm, 25.0 cm. and 30.0 cm. The actual length of an energy delivery device 16 depends on the location of the selected tissue mass to be ablated, its distance from the skin, its accessibility as well as whether or not the physician chooses a laparoscopic, percutaneous or other procedure.

An insulation sleeve 18 may be positioned around an exterior of introducer 14 and/or energy delivery devices 16 and 17. All or some of insulation sleeves 18 may be adjustably positioned so that the length of an energy delivery device electromagnetic energy delivery surface can be varied. Each insulation sleeve 18 surrounding an introducer 14 can include one or more apertures. This permits the introduction of an energy delivery device 16 through introducer 14 and insulation sleeve 18.

In one embodiment, insulation sleeve 18 comprises a polyamide material. A sensor 24 may be positioned on top of polyimide insulation sleeve 18. The polyamide insulation sleeve 18 is semi-rigid. Sensor 24 can lay down substantially along the entire length of polyamide insulation sleeve 18. Introducer 14 is made of a flexible material. Energy delivery devices 16 and 17 have distal ends 16' and 17' respectively, that are made of NiTi hypodermic tubing. A handpiece may be included with markings to show the length of lateral deployment of energy delivery devices 16 from introducer 14.

An electromagnetic energy source 20 is configured to be coupled to cell necrosis apparatus 12 with one or more cables 22. Electromagnetic energy source 20 can be RF, microwave, short wave, laser and the like. Cell necrosis apparatus 12 can be comprised of energy delivery devices 16 that are RF electrodes, microwave antennas, as well as combinations thereof. Electromagnetic energy source 20 may be a combination RF/microwave box. Further a laser optical fiber, coupled to a laser source 20 can be introduced through one or both of introducer 14 or a energy delivery device 16 and 17. Introducer 14 and/or an energy delivery device 16 and 17 can be an arm for the purposes of introducing the optical fiber. Energy delivery devices 16 and 17 are electromagnetically coupled to electromagnetic energy source 20. The coupling can be direct from electromagnetic energy source 20 to each energy delivery device 16, or indirect by using a collet, sleeve and the like which couples one or more energy delivery devices 16 and 17 to electromagnetic energy source 20. Electromagnetic energy can be delivered from one energy delivery device 16 and 17 to another.

One or more sensors 24 may be positioned on at least a portion of interior or exterior surfaces of introducer 14, energy delivery devices 16 and 17, or insulation sleeve 18. Preferably sensors 24 are positioned at introducer distal end 14', energy delivery device distal ends 16' and 17', and insulation sleeve distal end 18'. Sensors 24 permit accurate measurement of temperature at a tissue site in order to determine, (i) the extent of cell necrosis, (ii) the amount of cell necrosis, (iii) whether or not further cell necrosis is needed and (iv) the boundary or periphery of the ablated mass. Further, sensors 24 prevent non-targeted tissue from being destroyed or ablated.

Sensors 24 are of conventional design, including but not limited to thermistors, thermocouples, resistive wires, and the like. Suitable thermal sensors 24 include a T type thermocouple with copper constantene, J type, E type, K type, fiber optics, resistive wires, thermocouple IR detectors, and the like. It will be appreciated that sensors 24 need not be thermal sensors.

Sensors 24 measure temperature and/or impedance to permit monitoring and a desired level of cell necrosis to be achieved without destroying too much tissue. This reduces damage to tissue surrounding the targeted mass to be ablated. By monitoring the temperature at various points within the interior of the selected tissue mass, a determination of the selected tissue mass periphery can be made, as well as a determination of when cell necrosis is complete. If at any time sensor 24 determines that a desired cell necrosis temperature is exceeded, then an appropriate feedback signal is received at electromagnetic energy source 20 which then regulates the amount of electromagnetic energy delivered to energy delivery devices 16 and 17.

The geometry of the cell necrosis mass is selectable and controllable. Any number of different cell necrosis geometries can be achieved. Creation of different cell necrosis geometries is dependent on the length of electromagnetic energy cell necrosis delivery surfaces, the number of energy delivery devices, the size of the electromagnetic delivery surfaces, the amount of power delivered to the energy delivery devices, and the duration of time for power delivery to the energy delivery devices.

Apertures 26 are formed at distal end 14' or formed in a side of an exterior of introducer 14. Apertures 26 provide for the advancement and/or retraction of energy delivery devices 16 and 17 to and from introducer 14.

In one embodiment, cell necrosis apparatus 12 includes a groundpad electrode 27 coupled to energy source 20. A sensor 24 is positioned at groundpad electrode 27 and is used to minimize patient burns on skin surfaces.

In another embodiment, a method for creating a volumetric cell necrosis in a selected tissue mass provides cell necrosis apparatus 12 including introducer 14 with an introducer lumen, a plurality of energy delivery devices 16 deployable from the lumen, and an electromagnetic energy source 20 coupled to the plurality of energy delivery devices. Introducer 14 is inserted into the selected tissue mass with the plurality of energy delivery devices positioned in the introducer 14 lumen. The plurality of energy delivery devices 16 are advanced from the introducer lumen to distend away from introducer 14 to surround a selected mass before or after introducer 14 has pierced the selected cell necrosis site. 5 to 200 watts, preferably 5 to 100, and still more preferably 5 to 50 watts of electromagnetic energy is delivered from electromagnetic energy source 20 to the plurality of energy delivery devices 16 without impeding out an energy delivery device of the plurality of energy delivery devices. The volumetric cell necrosis is created between the plurality of energy delivery devices 16.

There is wide variation in the amount of deflection of energy delivery device 16. For example, energy delivery device 16 can be deflected a few degrees from the longitudinal axis of introducer 14, or energy delivery devices 16 can be deflected in any number of geometric configurations. Further, energy delivery devices 16 are capable of being introduced from introducer 14 a few millimeters from introducer 14, or a much larger distance. In one embodiment, a distal portion of introducer 14 can also be an electromagnetic energy delivery surface.

Figure 2:
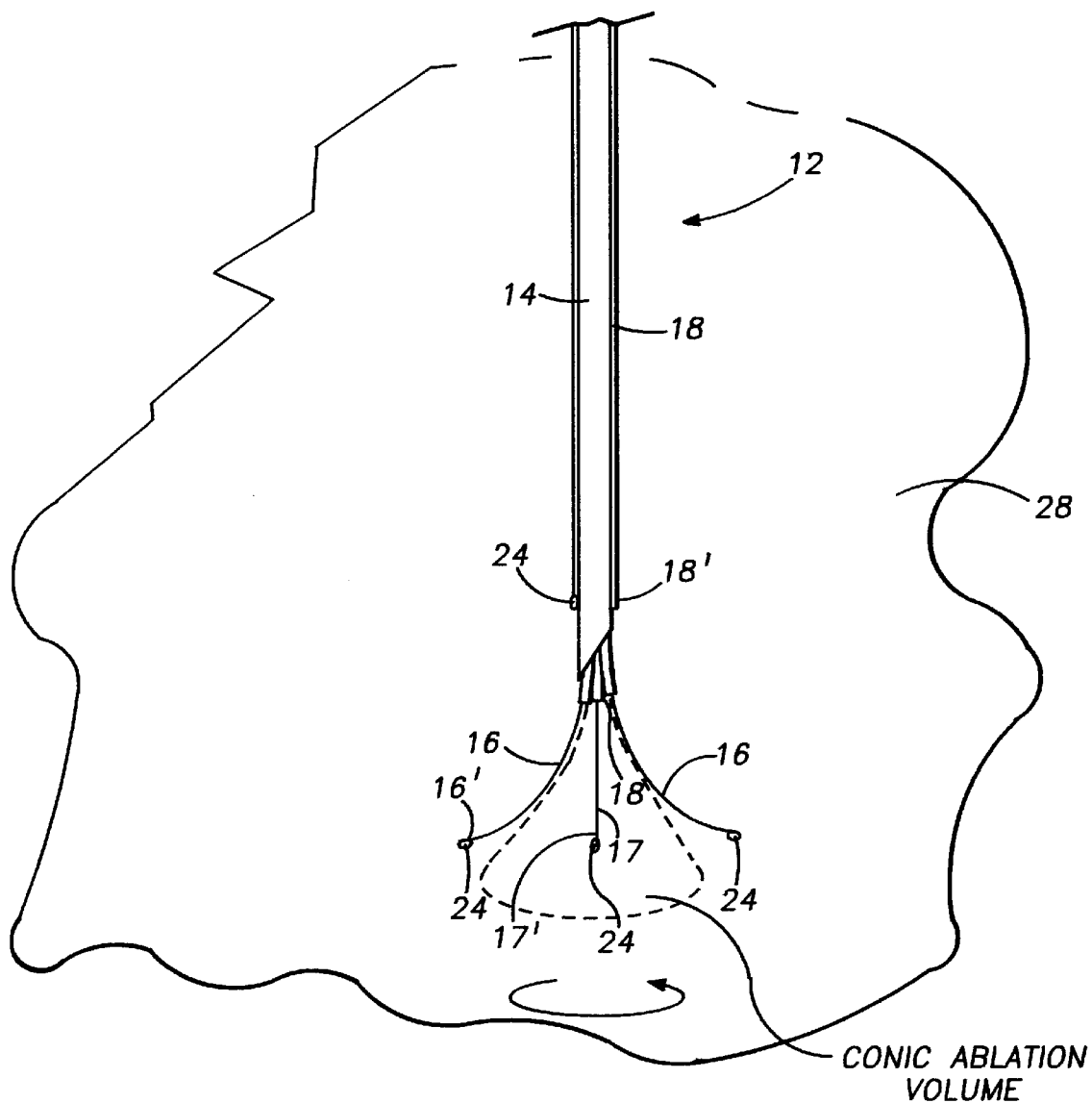
FIG. 2 is a perspective view of a conic geometric ablation achieved with the apparatus of FIG. 1.

As illustrated in FIG. 2, introducer 14 is introduced into a selected tissue mass 28. Two or more energy delivery devices 16 and energy delivery device 17 are positionable within an introducer lumen. In various embodiments, 3, 4, 5, or 6 energy delivery devices 16 are introduced laterally through introducer 14. Subsequently, energy delivery device distal ends 16' and 17' are advanced out of aperture 26 into selected tissue mass 28. When insulation sleeves 18 are included they can be adjusted for energy delivery devices 16 and 17. RF, microwave, short wave and the like energy is delivery to energy delivery device 16 in a monopolar mode (RF), or alternatively, cell necrosis apparatus 12 can be operated in a bipolar mode (RF). Cell necrosis apparatus 12 can be switched between monopolar and bipolar operation and may have multiplexing capability between different energy delivery devices 16. Energy delivery device distal ends 16' and 17' are retracted back into introducer 14, and introducer 14 is then rotated. Energy delivery device distal ends 16' and 17' are then introduced into selected tissue mass 28. Energy delivery devices 16 and 17 may be introduced a short distance into selected tissue mass 28 to ablate a small area, e.g., 3 cm or less. It can then be advanced further into any number of times to create more cell necrosis zones. Again, energy delivery device distal ends 16' and 17' are retracted back into introducer 14, and introducer 14 can be, (i) rotated again, (ii) moved along a longitudinal axis of selected tissue mass 28 to begin another series of cell necrosis zones with energy delivery device distal ends 16' and 17' being introduced and retracted in and out of introducer 14, or (iii) removed from selected tissue mass 28. A number of parameters permit cell necrosis of selected tissue masses 28 of different sign and shapes including a series of cell necrosis zones having energy delivery devices 16 and 17 with variable length electromagnetic energy delivery surfaces and the use of one or more sensors 24.

Figure 3:
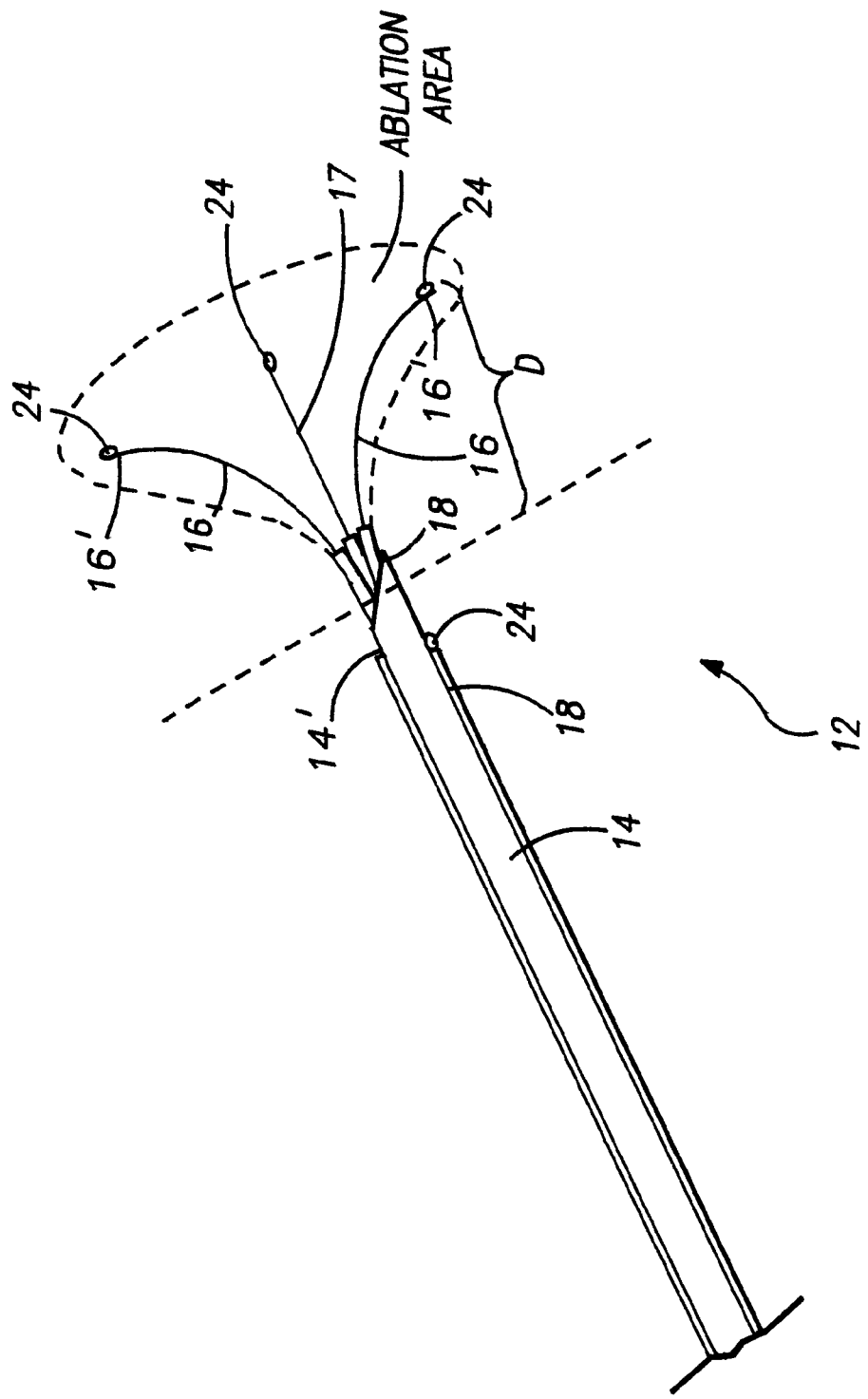
FIG. 3 is a perspective view of the cell necrosis apparatus of the present invention with two deployed energy delivery devices with curvature.

In FIG. 3, two energy delivery devices 16 are each deployed out of distal end 14' and introduced into selected tissue mass 28. In this embodiment, energy delivery devices 16 and 17 form a plane. The area of cell necrosis extends between the electromagnetic energy delivery surfaces of energy delivery devices 16 and 17. Energy delivery devices 17 are deployed a length of "D". Along the length of "D", an energy delivery device 16 energy delivery surface does not come back upon itself.

Introducer 14 can be introduced in an adjacent relationship to selected tissue mass 28. This particular deployment is useful for small selected tissue masses 28, or where piercing selected tissue mass 28 is not desirable. Introducer 14 can be rotated, with energy delivery devices 16 and 17 retracted in the lumen of introducer 14, and another cell necrosis volume defined between the energy delivery devices 16 and 17 is created. Further, introducer 14 can be withdrawn from its initial position adjacent to selected tissue mass 28, repositioned to another position adjacent to selected tissue mass 28, and energy delivery devices 16 and 17 deployed to begin another cell necrosis cycle. Any variety of different positions may be utilized to create a desired cell necrosis geometry for selected tissue mass of different geometries and sizes.

Figure 4:
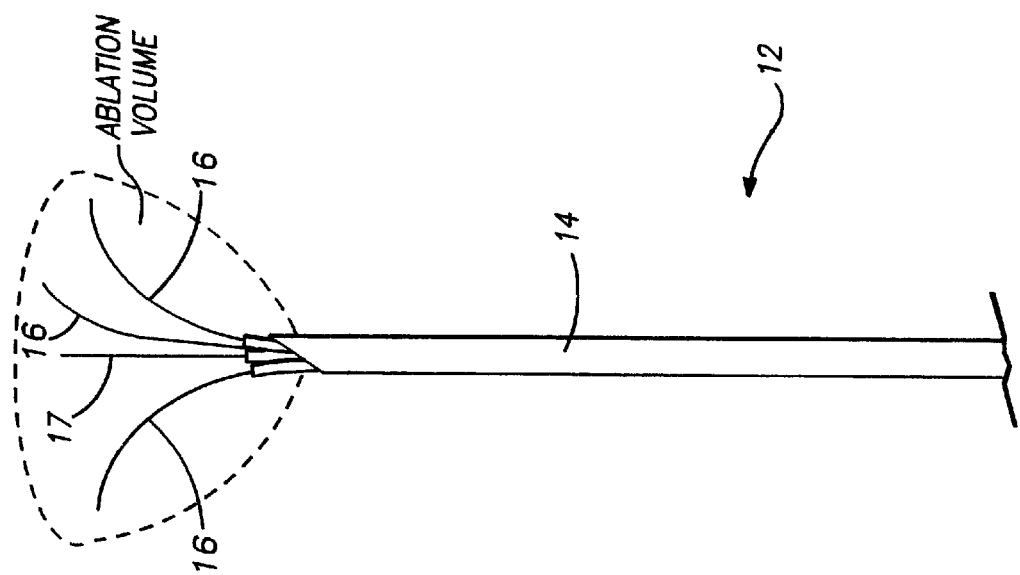
FIG. 4 is a perspective view illustrating three deployed energy delivery devices with curvature creating a complete cell necrosis volume.

In FIG. 4, three energy delivery devices 16 and 17 are introduced into selected tissue mass 28. The effect is the creation of a substantially complete cell necrosis volume formed between energy delivery devices 16 and 17 with a central core that is totally ablated.

Referring now to FIG. 5, a center of selected tissue mass 28 is pierced by introducer 14, energy delivery devices 16 and 17 are laterally deployed and retracted, introducer 14 is rotated, energy delivery devices 16 and 17 are deployed and retracted, and so on until a cylindrical cell necrosis volume is achieved. Cell necrosis apparatus 12 can be operated in the bipolar mode between the two energy delivery devices 16 and 17. In the embodiment where introducer 14 is also an electrode, cell necrosis is created between energy delivery device 16 and 17 and introducer 14. Alternatively, cell necrosis apparatus 12 can be operated in a monopolar mode.

Energy delivery devices 16 can serve the additional function of anchoring cell necrosis apparatus 12 in a selected mass, as illustrated in FIGS. 6(a). In FIG. 6(a) one or both energy delivery devices 16 are used to anchor and position introducer 14. Further, one or both energy delivery devices 16 are also used to ablate tissue.

FIG. 6(b) illustrates the infusion capability of cell necrosis apparatus 12. Two energy delivery devices 16 and energy delivery device 17 are positioned in a central lumen 14" of introducer 14. One or more of the energy delivery devices 16 can also include a central lumen coupled to an infusion source. Central lumen 14" is coupled to an infusion source and delivers a variety of infusion mediums to selected places both within and outside of the targeted cell necrosis mass. Suitable infusion mediums include but are not limited to, therapeutic agents, conductivity enhancement mediums, contrast agents or dyes, and the like. An example of a therapeutic agent is a chemotherapeutic agent. Each of the energy delivery devices 16, 17 as well as introducer 14 can introducer the infusion medium.

Figure 7:
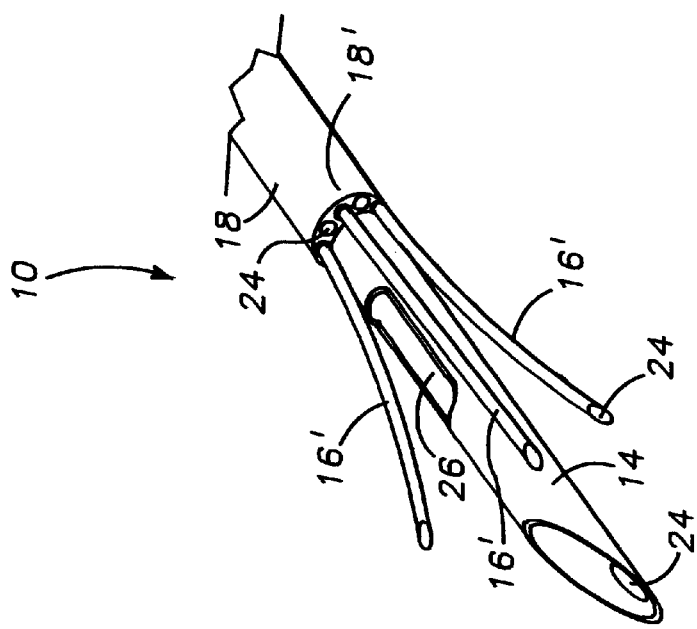
FIG. 7 is a perspective view of the cell necrosis apparatus of the present invention illustrating the deployment of three deployed energy delivery devices from a distal end of the insulation sleeve surrounding the introducer.

As shown in FIG. 7, insulation sleeve 18 can include one or more lumens for receiving energy delivery devices 16 which are deployed out of an insulation sleeve distal end 18'.

Figure 8:
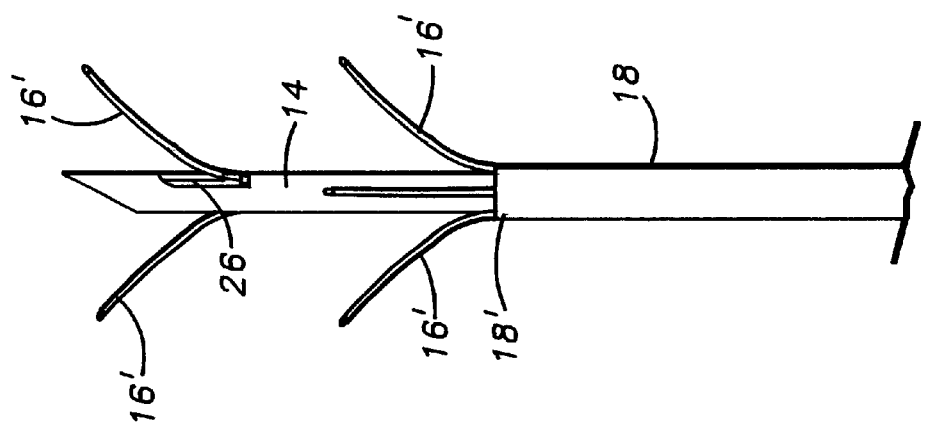
FIG. 8 is a perspective view of the cell necrosis apparatus of the present invention illustrating the deployment of two energy delivery devices with curvature from side ports formed in the introducer, and the deployment of two energy delivery devices with curvature from the distal portion of the introducer.

FIG. 8 illustrates two energy delivery devices 16 being introduced out of insulation sleeve distal end 18', and two energy delivery devices 16 introduced through apertures 26 formed in introducer 14. As illustrated, energy delivery devices 16 introduced through apertures 26 provide an anchoring function. FIG. 8 illustrates that energy delivery devices 16 can have a variety of different geometric configurations in cell necrosis apparatus 12.

Figure 9:
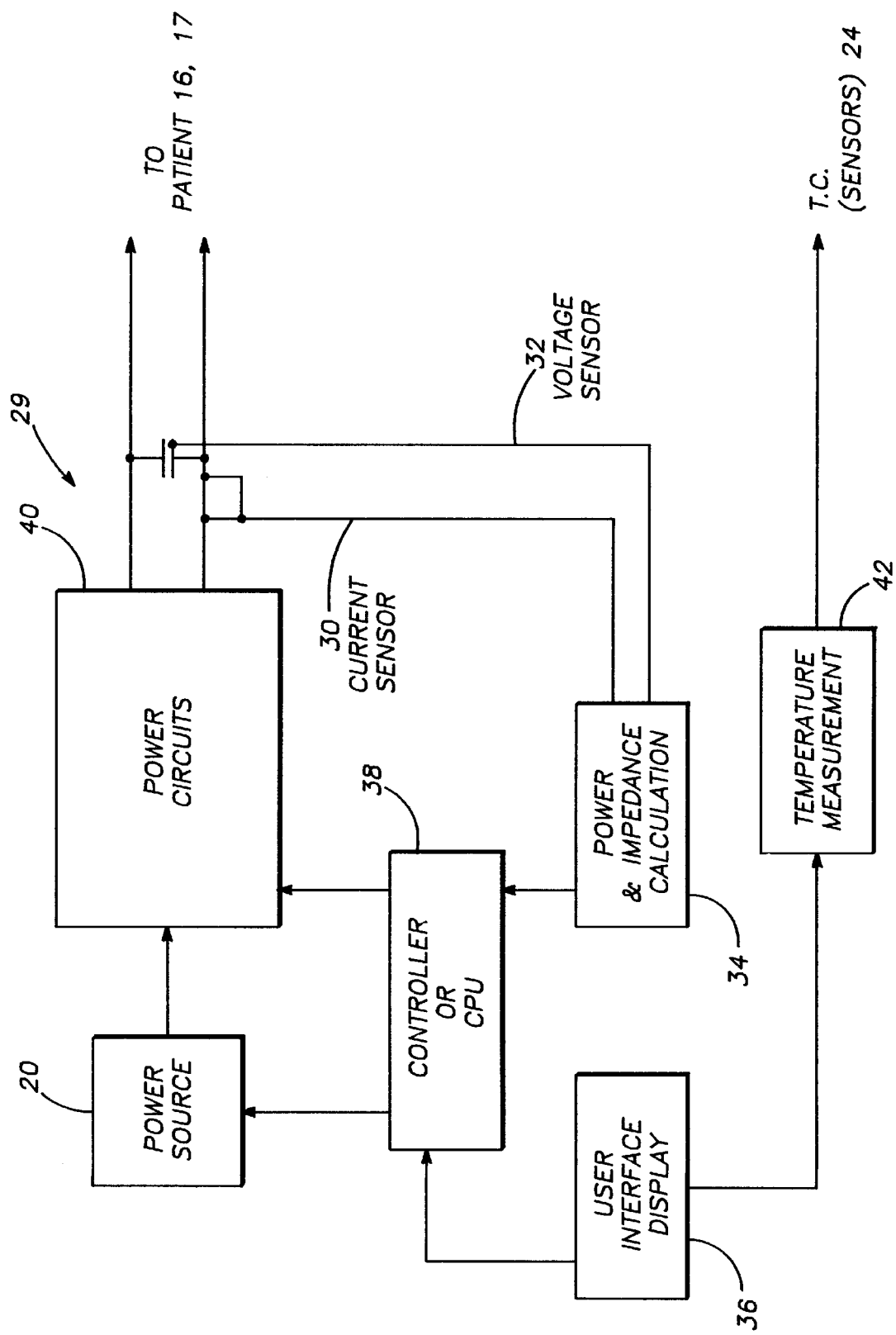
FIG. 9 is a block diagram illustrating the inclusion of a controller, electromagnetic energy source and other electronic components of the present invention.

Referring now to FIG. 9, a feedback control system 29 is connected to electromagnetic energy source 20, sensors 24 and energy delivery devices 16 and 17. Feedback control system 29 receives temperature or impedance data from sensors 24 and the amount of electromagnetic energy received by energy delivery devices 16 and 17 is modified from an initial setting of cell necrosis energy output, cell necrosis time, temperature, and current density (the "Four Parameters"). Feedback control system 29 can automatically change any of the Four Parameters. Feedback control system 29 can detect impedance or temperature and change any of the four parameters. Feedback control system 29 can include a multiplexer to multiplex different energy delivery devices, a temperature detection circuit that provides a control signal representative of temperature or impedance detected at one or more sensors 24. A microprocessor can be connected to the temperature control circuit.

The following discussion pertains particularly to the use of an RF energy source and RF electrodes but applies to other energy delivery devices and energy sources including but not limited to microwave, ultrasound, resistive heating, coherent and incoherent light, and the like.

Referring now to FIG. 9, all or portions of feedback control system 29 are illustrated. Current delivered through energy delivery devices 16 and 17 is measured by current sensor 30. Voltage is measured by voltage sensor 32. Impedance and power are then calculated at power and impedance calculation device 34. These values can then be displayed at user interface and display 36. Signals representative of power and impedance values are received by controller 38.

A control signal is generated by controller 38 that is proportional to the difference between an actual measured value, and a desired value. The control signal is used by power circuits 40 to adjust the power output in an appropriate amount in order to maintain the desired power delivered at energy delivery devices 16 and 17.

In a similar manner, temperatures detected at sensors 24 provide feedback for determining the extent of cell necrosis, and when a completed cell necrosis has reached the physical location of sensors 24. The actual temperatures are measured at temperature measurement device 42 and the temperatures are displayed at user interface and display 36. A control signal is generated by controller 38 that is proportional to the difference between an actual measured temperature, and a desired temperature. The control signal is used by power circuits 40 to adjust the power output in an appropriate amount in order to maintain the desired temperature delivered at the respective sensor 24. A multiplexer can be included to measure current, voltage and temperature, at the numerous sensors 24, and energy is delivered to energy delivery devices 16 and 17.

Controller 38 can be a digital or analog controller, or a computer with software. When controller 38 is a computer it can include a CPU coupled through a system bus. On this system can be a keyboard, a disk drive, or other non-volatile memory systems, a display, and other peripherals, as are known in the art. Also coupled to the bus are a program memory and a data memory.

User interface and display 36 includes operator controls and a display. Controller 38 can be coupled to imaging systems, including but not limited to ultrasound, CT scanners, X-ray, MRI, mammographic X-ray and the like. Further, direct visualization and tactile imaging can be utilized.

The output of current sensor 30 and voltage sensor 32 is used by controller 38 to maintain a selected power level at energy delivery devices 16 and 17. The amount of RF energy delivered controls the amount of power. A profile of power delivered can be incorporated in controller 38, and a preset amount of energy to be delivered can also be profiled.

Circuitry, software and feedback to controller 38 result in process control, and the maintenance of the selected power, and are used to change, (i) the selected power, including RF, microwave, laser and the like, (ii) the duty cycle (on-off and wattage), (iii) bipolar or monopolar energy delivery and (iv) infusion medium delivery, including flow rate and pressure. These process variables are controlled and varied, while maintaining the desired delivery of power independent of changes in voltage or current, based on temperatures monitored at sensors 24.

Figure 10:
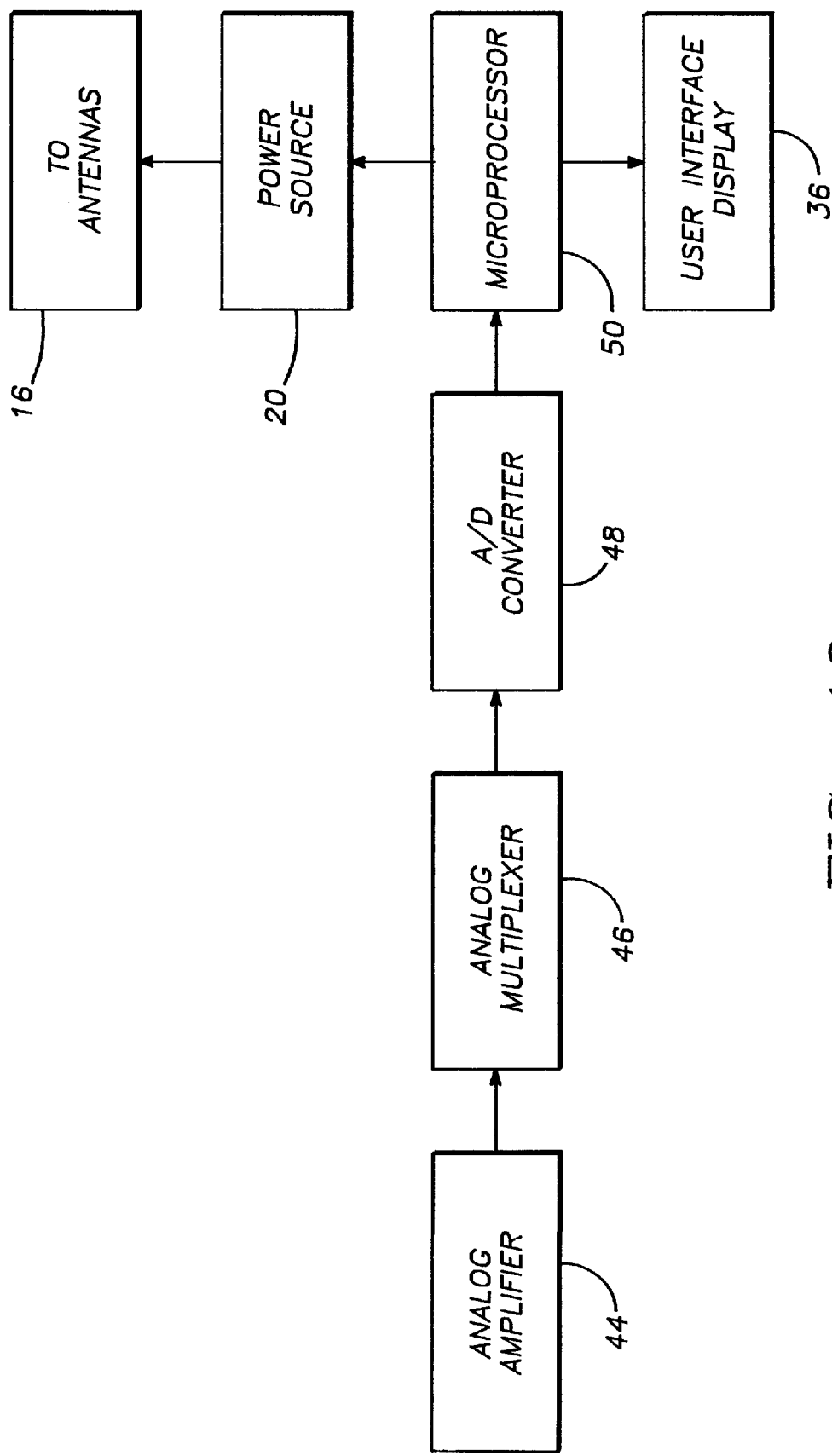
FIG. 10 is a block diagram illustrating an analog amplifier, analog multiplexer and microprocessor used with the present invention.

Referring now to FIG. 10, current sensor 30 and voltage sensor 32 are connected to the input of an analog amplifier 44. Analog amplifier 44 can be a conventional differential amplifier circuit for use with sensors 24. The output of analog amplifier 44 is sequentially connected by an analog multiplexer 46 to the input of A/D converter 48. The output of analog amplifier 44 is a voltage which represents the respective sensed temperatures. Digitized amplifier output voltages are supplied by A/D converter 48 to a microprocessor 50. Microprocessor 50 may be Model No. 68HCII available from Motorola. However, it will be appreciated that any suitable microprocessor or general purpose digital or analog computer can be used to calculate impedance or temperature.

Microprocessor 50 sequentially receives and stores digital representations of impedance and temperature. Each digital value received by microprocessor 50 corresponds to different temperatures and impedances.

Calculated power and impedance values can be indicated on user interface and display 36. Alternatively, or in addition to the numerical indication of power or impedance, calculated impedance and power values can be compared by microprocessor 50 with power and impedance limits. When the values exceed predetermined power or impedance values, a warning can be given on user interface and display 36, and additionally, the delivery of RF energy can be reduced, modified or interrupted. A control signal from microprocessor 50 can modify the power level supplied by electromagnetic energy source 20.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A cell necrosis apparatus, comprising:
   an introducer with a distal end sufficiently sharp to penetrate tissue; and
   an energy delivery device including a first RF electrode, a second RF electrode and a third RF electrode, each of the RF electrodes having a tissue piercing distal end, the first and second RF electrodes being positionable in the introducer as the introducer is advanced through tissue and deployable with curvature in an expanded state from the introducer, and the third RF electrode being positionable in the introducer as the introducer is advanced through tissue and deployable from the introducer in an expanded state with less curvature than the first or second RF electrodes, wherein in the expanded state a majority of the third RF electrode deployed in tissue has an energy delivery surface.

2. The apparatus of claim 1, wherein the third electrode is deployable from the introducer substantially without curvature.

3. The apparatus of claim 1, further comprising:
   an RF electrode advancement member coupled to the first, second and third RF electrodes and configured to advance the first, second and third RF electrodes through tissue.

4. The apparatus of claim 1, wherein the introducer is configured to receive a fluidic medium.

5. The apparatus of claim 1, wherein the first RF electrode includes a hollow lumen configured to receive a fluidic medium.

6. The apparatus of claim 1, wherein the second RF electrode includes a hollow lumen configured to receive a fluidic medium.

7. The apparatus of claim 1, further comprising:
   an insulator positioned in a surrounding relation to at least a portion of the introducer.

8. The apparatus of claim 1, further comprising:
   an insulator positioned in a surrounding relation to at least a portion of the first RF electrode.

9. The apparatus of claim 8, further comprising:
   an insulator positioned in a surrounding relation to at least a portion of the second RF electrode and an insulator positioned in a surrounding relation to at least a portion of the third RF electrode.

10. The apparatus of claim 1, further comprising:
    a sensor coupled to the first RF electrode.

11. The apparatus of claim 10, wherein the sensor is a thermal sensor.

12. The apparatus of claim 1, further comprising:
a sensor coupled to the introducer.

13. The apparatus of claim 1, wherein the first RF electrode is formed of a shaped memory alloy.

14. The apparatus of claim 1, wherein the first RF electrode is formed of stainless steel.

15. The apparatus of claim 1, wherein the first and second RF electrodes are deployable to surround a selected tissue site.

16. The apparatus of claim 15, wherein the first and second RF electrodes are deployable to surround a tumor.

17. The apparatus of claim 10, further comprising:
a feedback control coupled to the sensor and to the first RF electrode.

18. The apparatus of claim 1, further comprising:
an impedance measurement apparatus coupled to the first RF electrode.

19. The apparatus of claim 18, wherein the impedance measurement apparatus comprises:
a controller;
a microprocessor coupled to the controller; and
a feedback control including circuitry, wherein RF energy is delivered to a tissue site, a measurement of a voltage and current of a tissue site are determined and the current adjusted according to the measurement of the voltage and current of the tissue site.

20. The apparatus of claim 1, wherein the introducer is a flexible introducer.

21. The apparatus of claim 1, wherein at least a portion of the introducer is an energy delivery device.

22. The apparatus of claim 1, wherein a distal portion of the introducer is an RF electrode.

23. A cell necrosis apparatus, comprising:
an introducer including a lumen and a distal end sufficiently sharp to penetrate tissue;
an energy delivery device including at least a first RF electrode with a tissue piercing distal portion, a second RF electrode with a tissue piercing distal portion and a third RF electrode with a tissue piercing distal portion, the first, second and third RF electrodes being positionable in the introducer as the introducer is advanced through tissue and deployable in an expanded state with curvature from the introducer at a selected tissue site, the third RF electrode being deployed from the introducer with less curvature than the first or second RF electrodes and the first and second RF electrodes exhibiting at least a first and a second radius of curvature when positioned at the selected tissue site wherein in the expanded state a majority of the third RF electrode deployed in tissue has an energy delivery surface; and
a groundpad electrode coupled to the first and second RF electrodes.

24. The apparatus of claim 23, further comprising: a first sensor coupled to the groundpad electrode.

25. The apparatus of claim 23, further comprising:
an RF electrode advancement member coupled to the first and second RF electrodes and configured to advance the first and second RF electrodes through tissue.

26. The apparatus of claim 23, wherein the introducer is configured to receive a fluidic medium.

27. The apparatus of claim 23, wherein the first RF electrode includes a hollow lumen configured to receive a fluidic medium.

28. The apparatus of claim 23, further comprising:
an insulator positioned in a surrounding relation to at least a portion of the introducer.

29. The apparatus of claim 23, further comprising:
an insulator positioned in a surrounding relation to at least a portion of the first RF electrode.

30. The apparatus of claim 23, further comprising:
an insulator positioned in a surrounding relation to at least a portion of the second RF electrode and an insulator positioned in a surrounding relation to at least a portion of the first and second RF electrodes.

31. The apparatus of claim 24, further comprising:
a second sensor coupled to the first RF electrode.

32. The apparatus of claim 31, wherein the second sensor is a thermal sensor.

33. The apparatus of claim 32, further comprising:
a third sensor coupled to the introducer.

34. The apparatus of claim 23, wherein the first RF electrode is formed of a shaped memory alloy.

35. The apparatus of claim 23, wherein the first RF electrode is formed of stainless steel.

36. The apparatus of claim 23, wherein the first and second RF electrodes are deployable to surround a selected tissue site.

37. The apparatus of claim 31, further comprising:
a feedback control coupled to the first sensor and the first RF electrode.

38. The apparatus of claim 23, further comprising:
an impedance measurement apparatus coupled to the first RF electrode.

39. The apparatus of claim 38, wherein the impedance measurement apparatus comprises:
a controller;
a microprocessor coupled to the controller; and
a feedback control including circuitry, wherein RF energy is delivered to a tissue site, a measurement of a voltage and current of a tissue site are determined and the current adjusted according to the measurement of the voltage and current of the tissue site.

40. The apparatus of claim 23, wherein the introducer is a flexible introducer.

41. The apparatus of claim 23, wherein at least a portion of the introducer is an energy delivery device.

42. The apparatus of claim 23, wherein a distal portion of the introducer is an RF electrode.

* * * * *